United States Patent [19]

Fraser-Reid et al.

[11] Patent Number: 5,476,924
[45] Date of Patent: Dec. 19, 1995

[54] PROTECTING GROUP FOR ACETALS AND METHODS OF USING THE SAME IN THE ACTIVATION OF SACCHARIDES

[75] Inventors: Bertram O. Fraser-Reid; David R. Mootoo; J. Cristobal Lopez, all of Durham, N.C.

[73] Assignee: Duke University, Durham, N.C.

[21] Appl. No.: 361,461

[22] Filed: Dec. 21, 1994

Related U.S. Application Data

[63] Continuation of Ser. No. 9,358, Jan. 26, 1993, abandoned, which is a continuation of Ser. No. 595,869, Oct. 10, 1990, abandoned, which is a continuation-in-part of Ser. No. 302,349, Jan. 27, 1989, abandoned.

[51] Int. Cl.$^6$ ............................ C07H 15/00; C07H 15/04
[52] U.S. Cl. ...................... 536/18.6; 536/4.1; 536/18.4; 536/18.5; 536/115; 536/119; 536/120; 546/1; 546/268; 546/283; 546/290; 546/292
[58] Field of Search .................................. 536/18.5, 18.4, 536/18.6, 4.1, 115, 119, 120; 546/1, 290, 292, 268, 283

[56] References Cited

U.S. PATENT DOCUMENTS

| | | | |
|---|---|---|---|
| 2,390,507 | 12/1945 | Cantor | 536/4.1 |
| 3,103,508 | 9/1963 | Fisher | 526/238.23 |
| 3,375,243 | 3/1968 | Nevin | 536/18.6 |
| 3,565,885 | 2/1971 | Molotsky | 536/18.6 |
| 4,284,763 | 8/1981 | Theiwall | 536/4.1 |
| 4,574,122 | 3/1986 | Kruger | 514/42 |
| 4,617,269 | 10/1986 | Rathbone | 435/97 |
| 4,631,272 | 12/1986 | Lockhoff | 514/23 |
| 4,680,287 | 5/1987 | Lockhoff | 514/42 |
| 4,683,222 | 5/1987 | Stadler | 514/42 |
| 4,699,899 | 10/1987 | Kruger | 514/42 |
| 4,713,447 | 12/1987 | Letton | 536/18.6 |
| 5,041,226 | 8/1991 | Shibata | 210/635 |

FOREIGN PATENT DOCUMENTS

| | | |
|---|---|---|
| 084999 | 8/1983 | European Pat. Off. . |
| 99183 | 1/1984 | European Pat. Off. . |
| 0113599 | 7/1984 | European Pat. Off. . |
| 0247428 | 12/1987 | European Pat. Off. . |
| 3617272 | 11/1987 | Germany . |

OTHER PUBLICATIONS

Iley et al, J. of Am. Chem. Soc., vol. 97, No. 9, pp. 2563–2565 (1975).
Mootoo et al, J. Am. Chem. Soc., vol. 110, pp. 5583–5584 (1988).
Konradsson et al J. Chem. Soc. Chem. Commun. 1990 p. 270.
Llera et al J. Org. Chem. 1990 55:2997.
Lemieux et al Canadian J. of Chem. 1964 12:532.
Fraser–Reid et al J. Chem. Soc. Chem. Commun. pp. 823–825 (1988).
Frechet et al J. Amer. Chem. Soc. 93:492 (1971).
Hanessian et al Carbohydrate Res. 53:C13 (1977).
Lemieux et al Canadian J. of Chem. 4495 (1987).
Fraser–Reid Can. J. Chem. 57:645 (1979).
Lemieux et al Canadian J. of Chem. 43:2190 (1965).
Fraser–Reid et al J. Carbohyd. Chem. 479 (1987).
Mootoo et al Carbohydrate Res. 174:99 (1988).
Capon Chem. Rev. 69:407 (1969).
Iley et al J. Am. Chem. Soc. 97:2563 (1975).
Shafizadeh Methods in Carbohy. Chem. 1:190 (1962).
Lemieux et al Can. J. of Chem. 42:539 (1964).
Mootoo et al J. Am. Chem. Soc. (1988) 110:2662–2663.
Schmidt et al Chemische Berichte (1960) pp. 556–557.
Morrison and Boyd Organic Chemistry (1966) pp. 1001–1014 and 1163.
McClard Tetrahedron Letters (1983) 24:2631–2634.
Dupuis et al J. Am. Chem. Soc. (1985) 107:4332–4433.
Protective Groups in Organic Chemistry Ed. by McOmie (1973) pp. 96–143.

*Primary Examiner*—David T. Fox
*Assistant Examiner*—Howard C. Lee
*Attorney, Agent, or Firm*—Nixon & Vanderhye

[57] ABSTRACT

The present invention relates to a method of protecting the hemiacetal or acetal group at the anomeric carbon of a saccharide molecule comprising forming a 4-alkenyl glycoside or 4-alkenoyl glycosyl ester. The invention also relates to use of 4-alkenyl glycosides and 4-alkenoyl glycosyl esters in carbohydrate chemistry, including in the synthesis of oligosaccharides.

9 Claims, 3 Drawing Sheets

PROTECTING GROUP FOR ACETALS AND METHODS OF USING THE SAME IN THE ACTIVATION OF SACCHARIDES

This invention was made with Government support under Grant No. CHE-8703916 awarded by the National Science Foundation. The Government has certain rights in this invention. This is a continuation of application Ser. No. 08/009,358, filed Jan. 26, 1993, now abandoned, which is a continuation of application Ser. No. 07/595,869, filed Oct. 10, 1990, now abandoned, which is a continuation-in-part of application Ser. No. 07/302,349, filed Jan. 27, 1989, now abandoned.

BACKGROUND OF THE INVENTION

The invention relates to methods in synthetic carbohydrate chemistry.

Carbohydrates or sugars are the most abundant class of organic compounds found in nature. They are also commercially important, especially in the food and drug industries.

Carbohydrates are divided into three classes of compounds: (1) monosaccharides or simple sugars such as glucose, fructose and galactose, which consist of a single saccharide unit; (2) disaccharides and oligosaccharides such as sucrose (glucose+fructose) or lactose (galactose+glucose), which consist of 2–10 saccharide units linked together; and (3) polysaccharides such as starch and cellulose, which have thousands of saccharide units linked together.

Monosaccharides are classified as aldoses, which in their straight chain form are aldehydes, and ketoses, which are ketones in their straight chain form. While a ketose forms a ring structure which has a hemiketal linkage, an aldose forms a ring structure which has a hemiacetal linkage.

For example, the aldose glucose forms the acetal, glucopyranose.

The carbonyl or hemiacetal carbon [carbon (1)] in aldoses is called the anomeric carbon. Disaccharides and oligosaccharides are formed when the anomeric carbon on one sugar molecule reacts with the hydroxyl group of another sugar molecule, or other alcohol, to form a glycosidic bond. The glycosidic bond may be α- or β- depending on the stereochemistry about the anomeric carbon.

Glycosides of aldoses and ketoses have the structure of acetals and ketals, respectively.

The oligosaccharides play key biological roles in humans. They are part of the glycoproteins which form the cell membrane in many tissues. In the last decade, it has become apparent that it is the "glyco" (i.e., the complex sugar) moiety rather than the "protein" moiety of glyoproteins that is of immunological importance. In addition, sugars are also important constituents of the nucleotides of deoxyribonucleic acids (DNA) and ribonucleic acids (RNA). The backbone of DNA and RNA is an alternating chain of pentose (sugar) and phosphate groups, to which purine and pyrimidine bases are attached.

The synthesis of complex sugars by linking one or more monosaccharide units together is of obvious importance to both academic and industrial chemistry. Glycosidation, a reaction of critical importance to all phases of carbohydrate chemistry, is the process of forming a glycoside (4) from a sugar molecule (1) (see reaction scheme below). In glycosidation reactions, the anomeric carbon must be converted into an electrophile, which requires activation by development of a good leaving group (—X or —OH$_2$) in order to generate a cyclic oxo-carbenium ion (3).

The problem encountered in this synthetic route is that it is difficult to perform other chemical transformations at other sites in the saccharide molecule. Such transformations cannot be carried out after the leaving group, —X or —OH$_2$, is formed at the anomeric carbon because the activated saccharide (2) is sensitive to most chemical reagents that would be used to accomplish transformations at other sites in the molecule. On the Other hand, if the leaving group is formed after such other transformations are performed, the other functionalities may be destroyed in the process of forming the leaving group.

SUMMARY OF THE INVENTION

Therefore, an object of the present invention is to provide a method for protecting the hemiacetal or acetal group at the anomeric center of a saccharide molecule.

Another object is to provide a protecting group which can withstand the action of other chemical reagents used to carry out transformations on sugar molecules.

Still another object is to provide a protecting group which can be easily and specifically cleaved in order to form a good leaving group at the anomeric carbon.

A further object of the invention is to provide synthetic methods for preparing glycosides, oligosaccharides, nucleosides, and glycoproteins by reacting a 4-alkenyl glycoside (or alkenoyl glycosyl ester) with (a) an alcohol to form an alkyl glycoside, (b) a partially protected sugar to form an oligosaccharide, (c) a heterocyclic base, such as a purine or pyrimidine, to form a nucleoside, or (d) a polypeptide to form a glycoprotein.

A still further object of the invention is to provide a method of oligosaccharide synthesis in which two saccharides can be specifically linked to form a single geometric isomer by activating and/or deactivating the starting saccharide molecules toward site specific addition.

Therefore, the invention provides a method for protecting the hemiacetal or acetal group at the anomeric carbon of a saccharide molecule by reacting the saccharide molecule with a 4-alkenyl alcohol (or 4-alkenoic acid) to form a 4-alkenyl glycoside (or 4-alkenoyl glycosyl ester in the case of the 4-alkenoic acid). Alternatively, a 4-substituted butyl alcohol can be used (see below).

The invention also provides 1-(4-alkenyl)glycosides (or 1-(4-alkenoyl)glycosyl esters), for example, those of formulae I–V (where "Pent" in the structures below represents a n-pentenyl (or n-pentenoyl in the case of the glycosyl ester) group):

wherein X is a heteroatom and $R_1$, $R_2$, $R_3$ and $R_4$ are independently alkyl groups having 1 to 8 carbon atoms, carbonyl groups having 2 to 8 carbon atoms, allyl, alcohol groups having 2 to 4 carbon atoms, cyclic alkyl groups having 4 to 7 carbon atoms, benzyl, methoxy benzyl, benzoyl, triphenylmethyl, tetrahydropyranyl (THP), trimethyl silyl, or tert-butyl-dimethylsilyl; $R_5$ and $R_6$ are both methyl or $R_5$ is hydrogen and $R_6$ is phenyl. The 1-(4-alkenyl)glycosides and 1-(4-alkenoyl)glycosyl esters of the invention can have as substituents at any one of positions 2–5 of the sugar, in addition to those indicated above, a carbon chain, branched or unbranched, so that a branched sugar is formed, or a nitrogen bearing substituent (in either case, the carbon or nitrogen atom is bonded directly to the sugar). In addition, the invention also provides 1-(4-substituted butyl and 4-alkenyl)glycosides and 1-(4-alkenoyl)glycosyl esters wherein said substituent at position 4 is a good leaving.

The invention further provides a method of alkyl glycoside synthesis which includes reacting a saccharide molecule with a 4-alkenyl alcohol to form a 4-alkenyl glycoside and then reacting the 4-alkenyl glycoside With a halonium-type compound or other electrophile in the presence of an alcohol to form an alkyl glycoside. Alternatively, the above-described 4-substituted butyl alcohol can be used in lieu of the 4-alkenyl alcohol. The above-described 4-alkenoyl glycosyl ester can also be reacted as above to form an alkyl glycoside.

The invention still further provides a method of oligosaccharide synthesis which includes reacting a saccharide molecule with a 4-alkenyl alcohol to form a 4-alkenyl glycoside and then reacting the 4-alkenyl glycoside with a halonium type compound in the presence of a sugar alcohol to form an oligosaccharide. Again, the above-described 4-substituted butyl alcohol can be used. Also, the above-described 4-alkenoic acid and corresponding 4-alkenoyl glycosyl ester can be used.

Also provided is a method of oligosaccharide synthesis in which the 1-(4-alkenyl)glycoside (or 1-(4-substituted butyl)glycoside) (or 1-(4-alkenoyl)glycerol ester) has an ether moiety at carbon-2 and the sugar alcohol has an ester group at carbon-2 in order to obtain the heterooligosaccharide product. (See Mootoo et al *J. Am. Chem. Soc.* 110:2662 (1988); Fraser-Reid et al. *J. Chem. Soc. Chem. Comm.* pp. 823–825 (1988); and Mootoo et al. *J. Am. Chem. Soc.* 110:5583 (1988).)

DETAILED DESCRIPTION OF THE INVENTION

In one embodiment of the method of the present invention, a 4-alkenyl alcohol is reacted with a saccharide molecule under conditions such that a 1-(4-alkenyl)saccharide is formed. The 1-(4-alkenyl)saccharide is then reacted with a halonium-type compound or other electrophile in the presence of an alcohol under conditions such that glycosidation occurs. The 4-alkenyl protecting group of the invention can include as few as 5 carbon atoms (i.e., n-pentenyl) or as many as thousands of carbon atoms, depending on the application (see, for example, Frechet et al. *J. Amer. Chem. Soc.* 93:492 (1971) where solid support of polymers is described). The structure of the 4-alkenyl protecting group, however, must be such that it is capable of forming, upon treatment of the 4-alkenyl glycoside with a halonium-type compound, the oxo-carbenium ion described below.

The method for protecting the hemiacetal or acetal group at the anomeric carbon of a saccharide molecule according to the invention may be carried out by a variety of procedures. (See Schmidt et al, *Chemische Berichte* 93:556 (1960)). Oxygen-containing saccharides are exemplified below, however, one skilled in the art will appreciate that saccharides containing any suitable heteroatom in the ring, for example, nitrogen, sulfur, or selenium, can also be used.

In one embodiment of the present invention, an O-protected saccharide molecule, used as the starting material, is glycosidated with a 4-alkenyl alcohol using protocols known in the art to give the corresponding 4-alkenyl glycoside. For example, the known sugar tetra-O-benzyl glucose can be glycosidated with n-pentenyl alcohol in acid to give the corresponding n-pentenyl glycoside (reaction (a) below; Bn=PhCH$_2$ and Pent=a n-pentenyl group) (see Example 1 for details).

Alternatively, the 1-bromo derivative of 2,3,4,6-tetra-O-acetylglucose or 2,3,4,6-tetra-O-acetylmannose can be reacted with n-pentenyl alcohol in the presence of silver triflate (AgOTf) (see: Hanessian et al *Carbohydrate Res.* 53:C13 (1977)) to yield 1-(n-pentenyl)-2,3,4,6-tetra-O-acetyl glucose (see reaction (b) below) and 1,2-[(n-pentenoxy)methylmethylidene]-3,4,6-tri-O-acetylmannose (see reaction (c) below), respectively. The latter product may be reacted with acid to give 1-(n-pentenyl)- 2,3,4,6-tetra-O-acetylmannose.

-continued (c)

A still further alternative is to react 1,2-dehydro-3,4,5-tri-O-protected sugar first with halogen and then with n-pentenyl alcohol in the presence of AgOTf (see: Lemieux and Fraser-Reid Can. J. of Chem. 43:1460 (1965)) (see reaction (d) below).

(d)

In another embodiment a N-protected saccharide molecule is used as the starting material, the nitrogen-containing substituent being, advantageously, a protected amine or a precursor of an amine, for example, a N-phthlimido or para-methoxy benzyldimino group. In a further embodiment, a branched sugar is used as the starting material. In a still further embodiment, a saccharide molecule is used as the starting material that has a halogen atom at one or more of positions 2, 3, 4 or 5.

In the 1-(4-alkenyl) glycosides of formulae I–V according to the invention, examples of X include oxygen, nitrogen, sulfur and selenium, and examples of $R_1$, $R_2$, $R_3$, and $R_4$ groups include methyl, ethyl, propyl, isopropyl, n-butyl, isobutyl, sec-butyl, tert-butyl, n-pentyl, isopentyl, amyl, tert-pentyl, acetyl, allyl, 2-hydroxyethyl, 3-hydroxypropyl, 2,3-dihydroxypropyl, 4-hydroxybutyl, cyclopentyl, benzyl, methoxy benzyl, benzoyl, triphenylmethyl, THP, trimethyl-silyl and tert-butyl-dimethylsilyl. $R_5$ and $R_6$ are both methyl or $R_5$ is hydrogen and $R_6$ is phenyl.

The 4-alkenyl glycosides of the present invention are stable toward reaction at the other sites in the saccharide molecule; yet upon treatment with halonium-type compounds, the 4alkenyl glycoside is chemospecifically transformed without the use of acid into an active intermediate, which reacts in situ to give the critical reactive oxo-carbenium ion:

Examples of suitable halonium-type compounds include bromine, N-bromosuccinimide (NBS), iodinium dicollidine perchlorate, and N-iodosuccinimide with an acid catalyst.

One skilled in the art will appreciate that 1-(4-substituted butyl)glycosides (wherein the substituent at position 4 is a good leaving group, such as a halogen atom, a trialkyl ammonium group, or a tosylate group) will, also give rise to the oxo-carbenium ion upon treatment with a halonium-type compound. Accordingly, such glycosides are also within the scope of the invention.

The 4-alkenyl glycoside can be reacted with a halonium-type compound or other electrophile in the presence of an alcohol or sugar alcohol in order to carry out a glycosidic exchange or to synthesize an oligosaccharide. The reaction may be carried out, for example, in a solvent such as acetonitrile, methylene chloride, or a mixture of methylene chloride and diethyl ether. If the alcohol is an alkanol, the product is an alkyl glycoside, and if the alcohol is another sugar, the product is an oligosaccharide.

An example of a general procedure for reacting 4-alkenyl glycosides, for example, n-pentenyl glycosides, with alkanols or sugar alcohols can be described schematically as follows:

1

-continued

As indicated above, the n-pentenyl glycoside (1 above) is resistant to a variety of chemical transformations. Various protecting groups, for example, Bn(PhCH$_2$), THP, t-BuMe$_2$Si, RCO, or methoxybenzyl, (i.e., R in 2 above) can be introduced using standard reactions well known in the art of carbohydrate chemistry (see for example Fraser-Reid et al J. Org. Chem. 52:4495 (1987) and Mootoo and Fraser-Reid Carbohydrate Res. 174:99 (1988)). Treatment with a halonium-type compound or other electrophile (X$^+$ above), having as a source, for example, Br$_2$, NBS, or iodinium dicollidine perchlorate, cleaves the pentenyl group, liberating the anomeric center chemospecifically to give 4a above.

Alternatively, if an alcohol, such as methanol, is used instead of water in the reaction mixture, glycoside exchange occurs which leads to the methyl glycoside 4b above. If another sugar (5 above) is incorporated in the reaction medium, the two sugars combine to give a disaccharide (6 above). Oligosaccharides can be produced in the same manner.

If the 4-alkenyl glycoside has an ester moiety at carbon-2, the 4-alkenyl glycoside is deactivated and reacts slowly at the anomeric carbon. If the 4-alkenyl glycoside has an ether moiety at carbon-2, the 4-alkenyl glycoside is activated and reacts more readily at the anomeric carbon than the deactivated form. Thus, a 4-alkenyl glycoside which is to act as an alcohol donor should have an ester at carbon-2, while an alcohol acceptor should have an ether at carbon-2.

Further, if a halogen is present at carbon-2, the 4-alkenyl glycoside is also an alcohol donor which reacts slowly at the anomeric carbon.

In addition to the foregoing, the present invention also relates to a method of protecting the hydroxyl group at the anomeric carbon in a saccharide which involves reacting the saccharide molecule with a 4-alkenoic acid (advantageously, n-pentenoic acid) under conditions such that a 4-alkenoyl glycosyl ester is formed. Such esters, in contrast to the glycosides described above, are sensitive to alkali and undergo reduction with reducing agents such as lithium aluminum hydride. Such differences can be exploited in that reaction conditions can, where desirable, be selected under which the glycosyl ester will react but the glycoside will not. One skilled in the art will appreciate that exploitation of these differences can lead to novel procedures for coupling reactions leading to, for example, oligosaccharides. The following scheme exemplifies this further embodiment of the invention:

glycosyl
n-pentenoate

+

-continued

Coupling of the glycosyl ester can be effected under the same conditions as can coupling of the glycoside.

The invention is further illustrated by the following non-limiting examples:

Example I

Glycogsidation with n-pentenyl alcohol

The n-pentenyl glycoside of formula:

(where Bn=PhCH$_2$ and Pent is a n-pentenyl group) was prepared by dissolving 9 g (50 mmol) of the sugar:

in 30 ml dimethylsulfoxide, together with 15 ml (150 mmol) 4-penten-1-ol and 100 mg camphorsulfonic acid. The solution was maintained at 100° C. After 15 h, 5 ml (50 mmol) 4-penten-1-ol was added and the reaction mixture stirred at 100° C. for 20 h. The reaction was quenched by adding 2 ml pyridine and the dimethylsulfoxide was removed under reduced pressure. The product was purified by silica gel chromatography (CH$_2$Cl$_2$:MeOH, 85:15) and analyzed by $^{13}$C NMR and $^1$H NMR, and subjected to standard benzylation conditions.

Example II

Preparation of an alkyl saccharide and a disaccharide

The n-pentenyl glycoside designated "2" in the following reaction scheme was prepared by Fischer glycosidation of tetra-O-benzyl glucose ("1" in scheme below) (see: Capon *Chem. Revs.* 69:407 (1969)). Reaction of compound ("2") with CH$_3$CN/MeOH/NBS gave an 85% yield of the methyl glycoside, "3" below.

When iodionium dicollidine perchlorate (see: Iley and Fraser-Reid *J. Am. Chem. Soc.* 97:2563 (1975); Fraser-Reid and Iley *Can. J. Chem.* 57:645 (1979); Lemieux and Morgan *Can. J. Chem.* 43:2190 (1965)) was used as an alternative source of halonium ion, the reaction time was substantially reduced (see Table I).

TABLE I

| solvent | X+ | time | yield | α:β |
|---|---|---|---|---|
| CH$_3$CN | NBS | 3 h | 85% | 1:3 |
| CH$_3$CN | I(collidine)$_2$ ClO$_4$ | 0.5 h | 75% | 1:3 |
| CH$_2$Cl$_2$ | " | 0.5 h | 85% | 1.2:1 |
| CH$_2$Cl$_2$/Et$_2$O (1:4) | " | 24 h | 75% | 3:1 |

The reaction of the sterochemically pure anomers (α and β of compound "2" in above scheme) in CH$_3$CN led to the same product composition of compound "3" in the above scheme. When CH$_2$Cl$_2$ and Et$_2$O were used as solvents (the insufficient solubility of iodonium salt in pure Et$_2$O made desirable the use of a 4:1 mixture of Et$_2$O/CH$_2$Cl$_2$), the results presented in Table I were obtained.

Figure 1:
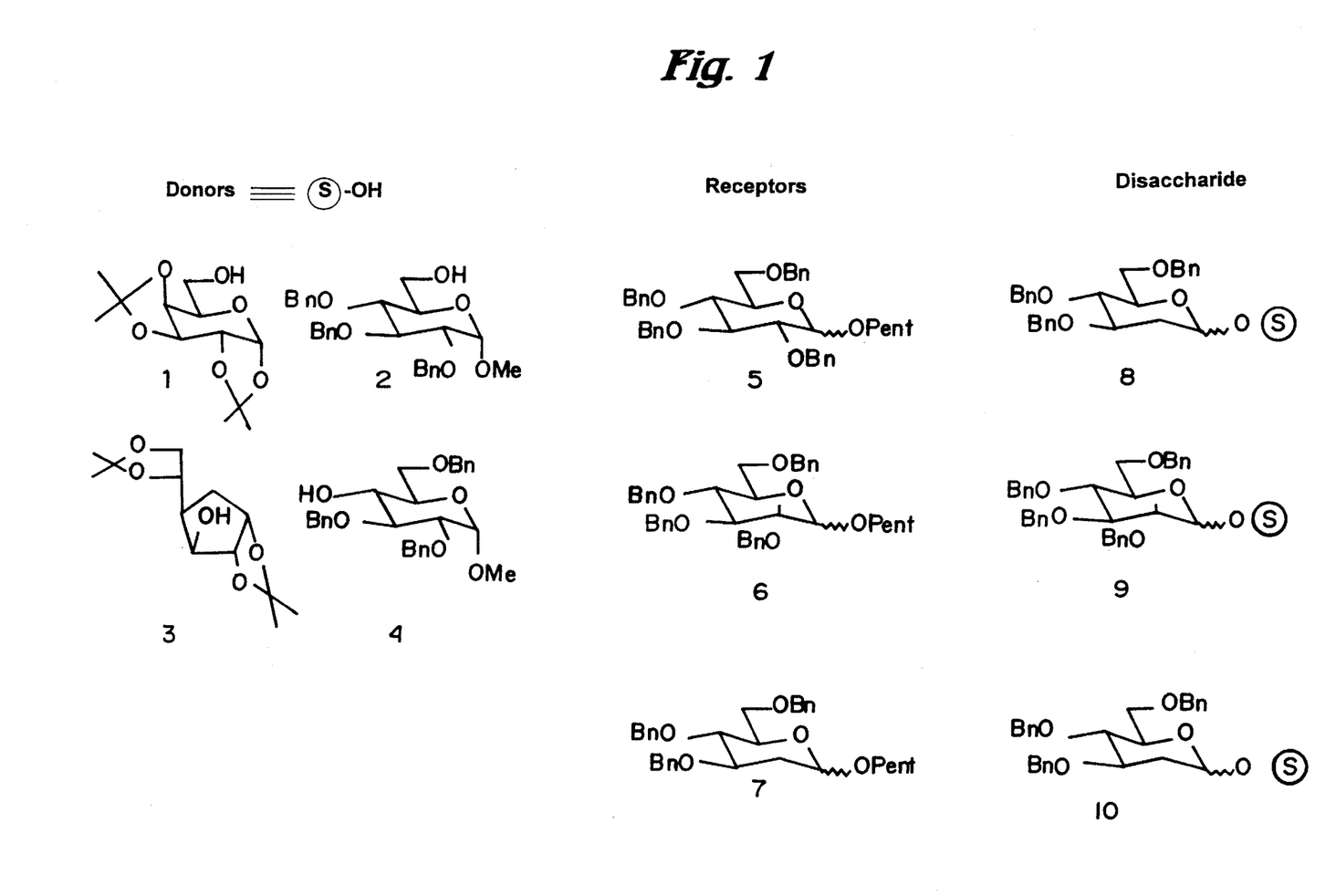
FIG. 1—Elaboration of n-pentenyl glycosides into disaccharides

When the monosaccharide alcohol donors "1" to "4" and receptors "5" to "7", shown in FIG. 1, were used, the results given in Table II were obtained.

TABLE II

| | | Solvent[a] | Disaccharides from (1)–(4)[b] | | | |
|---|---|---|---|---|---|---|
| Entry | Substrate | Time (hours) | percent | yield | (α:β ratio) | |
| | | | (8a) | (8b) | (8c) | (8d) |
| i | (5) | A (1–2) | 50 (1:4) | 56 (1:4) | 20 (2:1) | 20 (1:2) |
| ii | | B (1–2) | 66 (1.2:1) | 93 (1:1.4) | 58 (3:1) | 75 (1.2:1) |
| iii | | C (16–24) | 76 (7:1) | 96 (7:1) | 86 (4:1) | 95 (3:1) |

TABLE II-continued

| Entry | Substrate | Solvent[a] Time (hours) | Disaccharides from (1)-(4)[b] percent yield (α:β ratio) | | | |
|-------|-----------|------------------------|---------|--------|---------|---------|
|       |           |                        | (9a)    | (9b)   | (9c)    | (9d)    |
| iv    | (6)       | A (2–5)                | 48 (1.3:1) | 70 (1:1) | 32 (1.4:1) | 36 (6:1) |
| v     |           | B (2–5)                | 71 (1:1)   | 88 (1:1) | 63 (7:1)   | 76 (9:1) |
| vi    |           | C (24)                 | 70 (2.4:1) | 94 (1:1.3) | 79 (α only) | 92 (α only) |
|       |           |                        | (10a)   | (10b)  | (10c)   | (10d)   |
| vii   | (7)       | A (0.5)                | 61 (2:1) | 52 (1:1) | 40 (5:1) | 51 (7:3) |
| viii  |           | B (0.5)                | 77 (2:1) | 73 (1:1) | 66 (5:1) | 57 (4:1) |
| ix    |           | C (4–6)                | 75 (4:1) | 70 (1:1) | 65 (5:1) | 61 (4:1) |

[a]A = $CH_3CN$; B = $CH_2Cl_2$; C = $Et_2O/CH_2Cl_2$ (4:1)
[b]Designations a–d are as follows:
⑤—OH
a  1
b  2
c  3
d  4

Example III
Effect of protecting group on C2 oxygen

Figure 2:
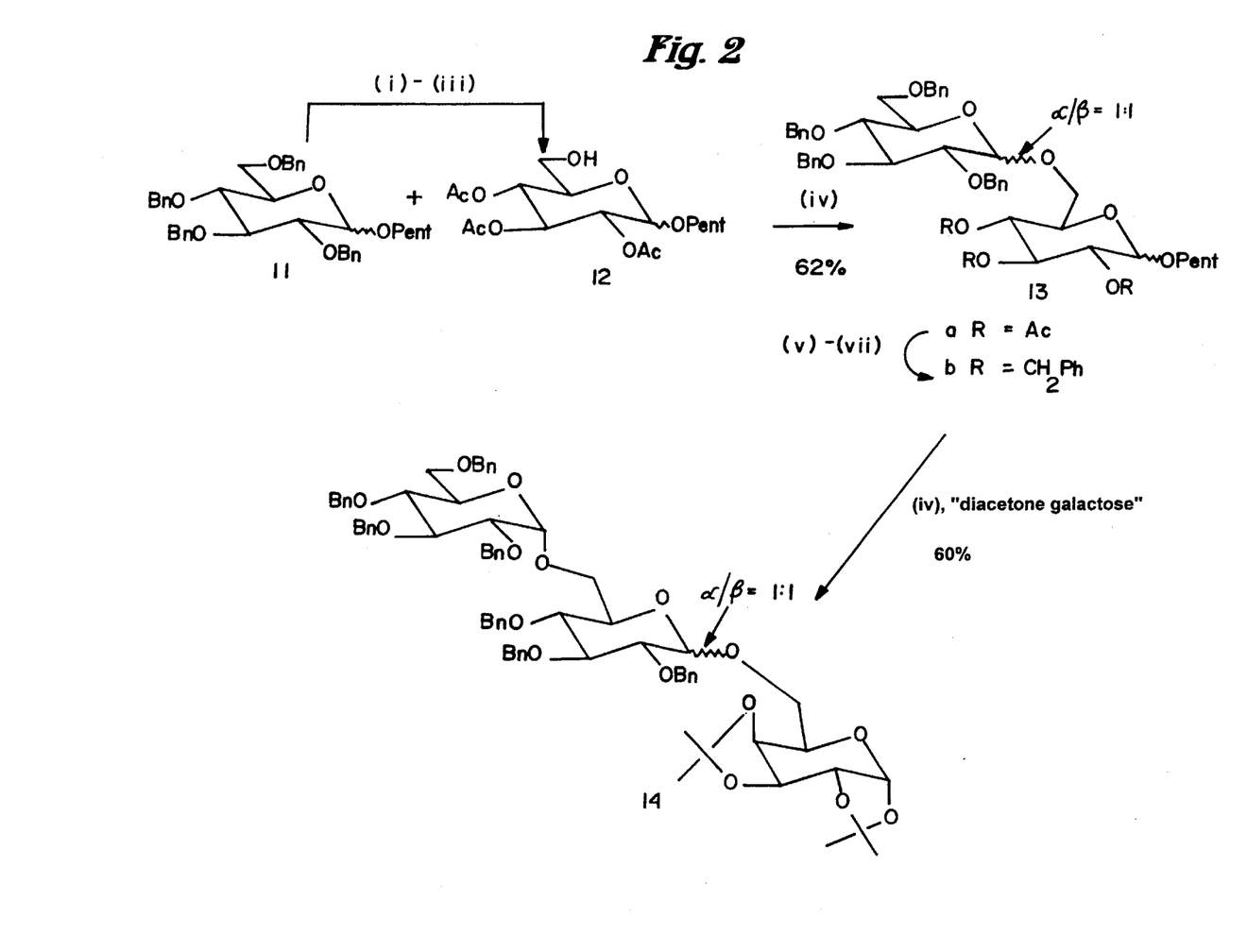
FIG. 2—Reaction scheme for formation of di- and trisaccharides

Referring to FIG. 2, the compound designated "11" was transformed to the primary alcohol "12" via standard procedures for Birch reduction, tritylation, acetylation, and detritylation (see, for example, Fraser-Reid et al. *J. Carbohydrate Chem.* 6:479 (1987) and *J. Org. Chem.* 52:4511 (1987)). The coupling of components designated "11" and "12" were mediated by iodonium dicollidine perchlorate (see Example II) (see also: Iley and Fraser-Reid *J. Am. Chem. Soc.* 97:2563 (1975); Fraser-Reid and Iley *Can. J. Chem.* 57:645 (1979); Lemieux and Morgan *Can. J. Chem.* 43:2190 (1965)). Specifically, iodonium dicollidine perchlorate (1.5 mmol) was added to a solution in dichloromethane (10 ml per mmol) of the "activated pentenyl glycoside" (1 mmol), and the "deactivated pentenyl glycoside" (1 mmol) and flame dried 4A molecular sieves. When the reaction was complete, as shown by thin layer chromatography, the mixture was diluted with dichloromethane and filtered through Celite. The filtrate, was washed with 10% aqueous sodium thiosulfate, saturated sodium bicarbonate solution, and brine. The solvent was dried ($MgSO_4$), filtered, and evaporated in vacuo. The products were purified by silica gel chromatography.

The yield of the disaccharide designated "13a" in FIG. 2 (1:1 ratio of α:β anomers) was 62%. Therefore, the 2-O acetyl group of "12" had "disarmed" the pentenyl glycoside, thereby ensuring that "11" served as the only glycosyl donor. There was no evidence for a hexaacetyl disaccharide arising from "12".

The anomers of "13a" were separated by chromatography and the n-pentenyl glycoside was "armed" via hydrolysis of the C2 ester of 13a and then benzylation of the resultant C2 alcohol to form "13b". Reaction of "13b" with "diacetone galactose" (1,2:3,4-di-O-isoproprylidene-α-D-galactopyranose; for preparation see: Shafizadeh, *Methods Carbohydr. Chem.* 1:193 (1962)) led to the trisaccharide "14" in 60% yield as a 1:1 ratio of α and β anomers at the newly formed anomeric center.

Figure 3:
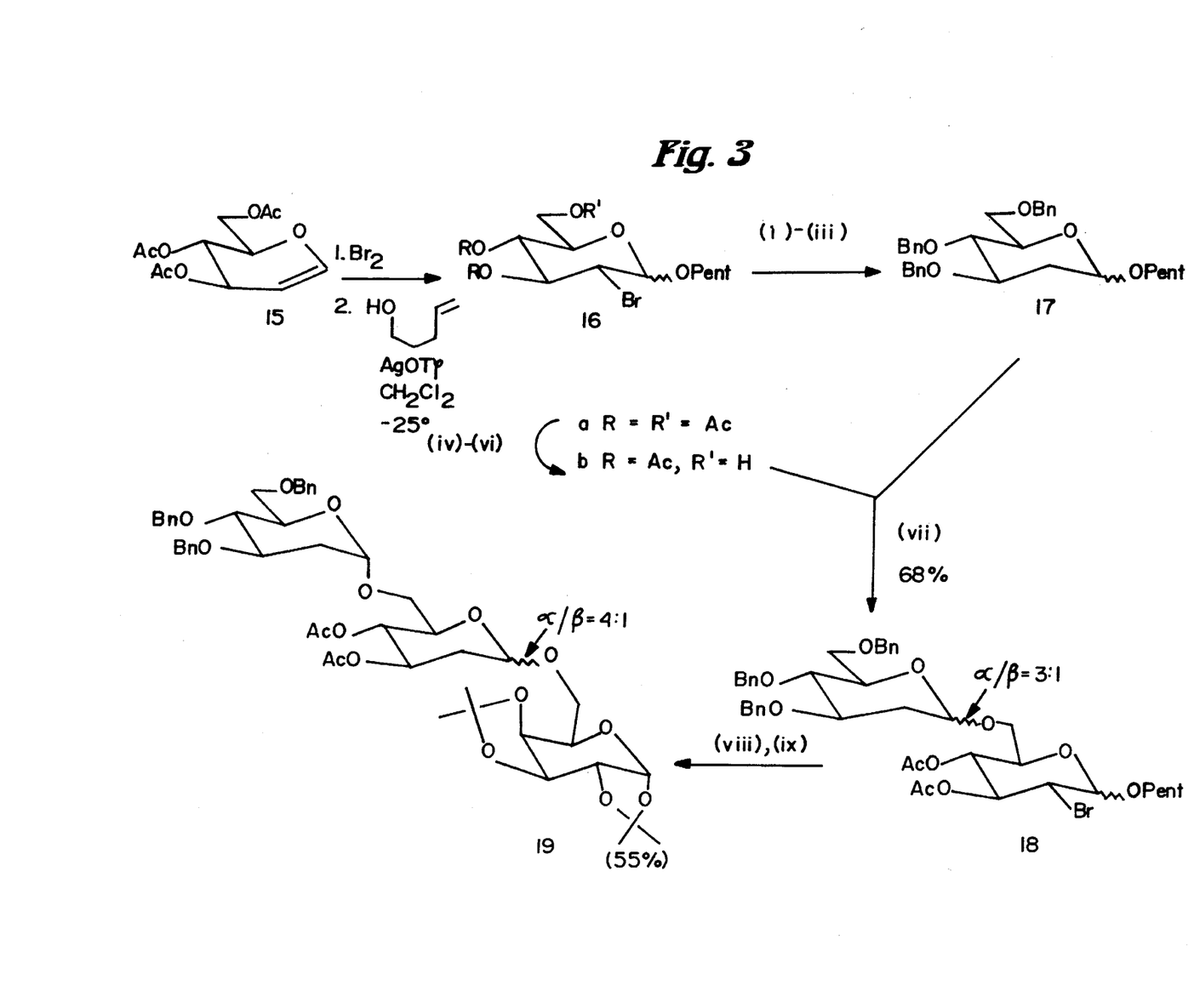
FIG. 3—Reaction scheme for formation of 2-deoxyoligosaccharides.

The production of the 2-deoxyglycoside of FIG. 3 involves the haloalkylation of glycals, designated "15"→"16" in FIG. 3 with subsequent reductive dehalogenation, "16"→"17" (Lemieux and Fraser-Reid *Can. J. Chem.* 42:532(1964); 42:539 (1964); 43:1460(1965)).

The 2-bromoalcohol (a disarmed n-pentenyl glycoside), "16b" of FIG. 3, and the 2-deoxyglycosyl donor "17" (an armed n-pentenyl glycoside), were subjected to saccharide coupling reaction conditions (step vii) (see above and Example II) to give a 68% yield of "18" (3:1 ratio of α:β anomers at the newly formed anomeric center) with no evidence of self-condensation of "16b". The α anomer was chromatographically separated and "armed" by reduction of the C2 bromine substituent using the procedure described earlier. The resultant 2-deoxy n-pentenyl glycoside disaccharide mixture was subjected to the standard saccharide coupling reaction conditions using diacetonegalactoside as the alcohol donor. The trisaccharide "19" was obtained in 55% yield as a 4:1 ratio of α:β anomers at the newly formed anomeric center.

For purposes of completing the background description and present disclosure, the entire contents of each of the published articles heretofore identified in this specification are hereby incorporated by reference into the specification and are relied upon.

The foregoing invention has been described in some detail for purposes of clarity and understanding. It will be clear to one skilled in the art to which the invention relates that the 1-(4-alkenyl)glycosides, as well as the 1-(4-substituted butyl)glycosides and 1-(4-alkenoyl)glycosyl esters, of the invention can have as substituents at any one of the positions 2–5 of the sugar, virtually any substituent. It will also be obvious that various combinations in form and detail can be made without departing from the scope of the invention.

What is claimed is:

1. A method of synthesizing a complex sugar comprising:
   (i) reacting a cyclic reducing sugar with a 4-alkenyl alcohol so that a 4-alkenyl glycoside is formed; and
   (ii) reacting said 4-alkenyl glycoside with a halonium compound in the presence of a sugar alcohol so that a glycosidic bond is formed between said reducing sugar and said sugar alcohol.

2. The method according to claim 1, wherein the halonium compound is selected from the group consisting of bromine, iodine, N-bromosuccinimide, N-iodosuccinimide and iodinium or bromonium containing salts.

3. The method according to claim 1, wherein the reaction in step (ii) is carried out in a solvent selected from the group consisting of acetonitrile, methylene chloride and a mixture of methylene chloride and diethyl ether.

4. The method according to claim 1, wherein said 4-alkenyl glycoside has an ether moiety at carbon-2 and the sugar alcohol has an ester moiety at carbon-2.

5. The method according to claim 1, wherein said 4-alkenyl alcohol is n-pentenyl alcohol.

6. A method of synthesizing a complex sugar comprising:
   (i) reacting a cyclic reducing sugar with 4-alkenoic acid so that a 1-(4-alkenoyl)glycosyl ester is formed; and
   (ii) reacting said glycosyl ester with a halonium compound in the presence of a sugar alcohol so that a glycosidic bond is formed between said reducing sugar and said sugar alcohol.

7. The method according to claim 6, wherein said 4-alkenoic acid is n-pentenoic acid.

8. A method of synthesizing a complex sugar comprising:
   reacting a 1-(4-alkenoyl)glycosyl ester, wherein said glycosyl moiety is derived from a cyclic reducing sugar, with a halonium compound in the presence of a sugar alcohol so that said complex sugar is formed.

9. The method according to claim 8 wherein said 4-alkenoic acid is n-pentenoic acid.

\* \* \* \* \*